(12) United States Patent
Akao (10) Patent No.: US 11,322,962 B2
(45) Date of Patent: May 3, 2022

(54) POWER SUPPLY UNIT FOR AEROSOL INHALER

(71) Applicant: JAPAN TOBACCO INC., Tokyo (JP)

(72) Inventor: Takeshi Akao, Tokyo (JP)

(73) Assignee: Japan Tobacco Inc., Tokyo (JP)

( * ) Notice: Subject to any disclaimer, the term of this patent is extended or adjusted under 35 U.S.C. 154(b) by 0 days.

(21) Appl. No.: 16/745,082

(22) Filed: Jan. 16, 2020

(65) Prior Publication Data

US 2020/0235600 A1    Jul. 23, 2020

Related U.S. Application Data

(60) Provisional application No. 62/793,551, filed on Jan. 17, 2019.

(30) Foreign Application Priority Data

Feb. 28, 2019   (JP) .............................. JP2019-035995

(51) Int. Cl.
*A24F 40/90* (2020.01)
*A24F 40/51* (2020.01)
(Continued)

(52) U.S. Cl.
CPC ............ *H02J 7/0068* (2013.01); *A24F 40/40* (2020.01); *A24F 40/50* (2020.01); *A24F 40/51* (2020.01); *A24F 40/53* (2020.01); *A24F 40/60* (2020.01); *A24F 40/90* (2020.01); *A24F 40/95* (2020.01); *A61M 15/009* (2013.01); *G05F 3/18* (2013.01);
(Continued)

(58) Field of Classification Search
CPC ..... A24F 47/008; A24F 40/46; H05B 1/0244; A24B 15/16
See application file for complete search history.

(56) References Cited

U.S. PATENT DOCUMENTS 8,997,753 B2 * 4/2015 Li ........................ H05B 1/0244
131/273
9,462,832 B2 * 10/2016 Lord ..................... A24F 47/008
(Continued)

FOREIGN PATENT DOCUMENTS

CN    203302350 U    11/2013
CN    203434232 U    2/2014
(Continued)

OTHER PUBLICATIONS

Decision to Grant Patent issued in related Japanese Patent Application No. 2019-035995 dated Jul. 16, 2019.
(Continued)

*Primary Examiner* — Jean F Duverne
(74) *Attorney, Agent, or Firm* — Venable LLP (57) ABSTRACT

A power supply unit for an aerosol inhaler includes: a power supply able to discharge power to a load for generating an aerosol from an aerosol generation source; a first circuit board including a resistor; and a second circuit board disposed apart from the first circuit board, and electrically connected to the first circuit board. The second circuit board includes at least one of: a control device configured to be able to control at least one of discharging and charging of the power supply; and a charging device configured to convert power which is input, into charging power for the power supply.

18 Claims, 9 Drawing Sheets

(51) Int. Cl.

| | |
|---|---|
| *A24F 40/60* | (2020.01) |
| *A24F 40/53* | (2020.01) |
| *A24F 40/50* | (2020.01) |
| *A24F 40/40* | (2020.01) |
| *A24F 40/95* | (2020.01) |
| *A24F 40/30* | (2020.01) |
| *H02J 7/00* | (2006.01) |
| *A61M 15/00* | (2006.01) |
| *H05K 1/18* | (2006.01) |
| *H05K 1/14* | (2006.01) |
| *G05F 3/18* | (2006.01) |
| *H01M 10/42* | (2006.01) |
| *H02J 7/04* | (2006.01) |
| *A61M 15/06* | (2006.01) |

(52) U.S. Cl.
CPC ........... *H01M 10/425* (2013.01); *H02J 7/005* (2020.01); *H02J 7/007* (2013.01); *H02J 7/0042* (2013.01); *H02J 7/0045* (2013.01); *H02J 7/0063* (2013.01); *H02J 7/007194* (2020.01); *H02J 7/04* (2013.01); *H05K 1/14* (2013.01); *H05K 1/181* (2013.01); *A24F 40/30* (2020.01); *A61M 15/0003* (2014.02); *A61M 15/06* (2013.01); *A61M 2205/3653* (2013.01); *A61M 2205/50* (2013.01); *A61M 2205/8206* (2013.01); *A61M 2205/8237* (2013.01); *A61M 2205/8243* (2013.01); *H05K 2201/10015* (2013.01); *H05K 2201/10022* (2013.01); *H05K 2201/10174* (2013.01)

(56) References Cited

U.S. PATENT DOCUMENTS

| | | | | |
|---|---|---|---|---|
| 10,154,691 | B2* | 12/2018 | Feldman | A24F 40/46 |
| 10,182,597 | B2* | 1/2019 | Schiff | A24F 47/008 |
| 10,368,581 | B2* | 8/2019 | Rostami | A61M 15/0003 |
| 10,433,580 | B2* | 10/2019 | Kobal | A24B 15/16 |
| 10,455,863 | B2* | 10/2019 | Rostami | A61M 15/06 |
| 10,645,971 | B2* | 5/2020 | Zitzke | A24F 47/008 |
| 2011/0304282 | A1* | 12/2011 | Li | A24F 47/008 |
| | | | | 315/362 |
| 2014/0278250 | A1 | 9/2014 | Smith et al. | |
| 2015/0128971 | A1* | 5/2015 | Verleur | H02J 7/00 |
| | | | | 131/329 |
| 2015/0173124 | A1 | 6/2015 | Qiu | |
| 2015/0208731 | A1* | 7/2015 | Malamud | H05B 1/0244 |
| | | | | 131/328 |
| 2016/0278432 | A1 | 9/2016 | Liu | |
| 2017/0250552 | A1 | 8/2017 | Liu | |
| 2019/0191782 | A1* | 6/2019 | Tang | A24F 40/46 |
| 2019/0261690 | A1 | 8/2019 | Lin et al. | |
| 2020/0113237 | A1 | 4/2020 | Smith et al. | |

FOREIGN PATENT DOCUMENTS

| | | |
|---|---|---|
| CN | 203597408 U | 5/2014 |
| CN | 104348214 A | 2/2015 |
| CN | 105307521 A | 2/2016 |
| CN | 206865186 U | 1/2018 |
| JP | 2017-127300 A | 7/2017 |
| WO | 2015/190810 A1 | 12/2015 |
| WO | 2018-068602 A1 | 4/2018 |

OTHER PUBLICATIONS

Office Action dated Jul. 20, 2020 in corresponding Taiwanese Patent Application No. 109101547.

Office Action dated Aug. 7, 2020 in Canadian Patent Application No. 3,068,701.

European Search Report issued in related European Patent Application No. 20152148.1 dated May 26, 2020.

Office Action dated Feb. 8, 2021, in Chinese Patent Application No. 202010051933.9.

* cited by examiner

POWER SUPPLY UNIT FOR AEROSOL INHALER

CROSS-REFERENCE TO RELATED APPLICATIONS

This application is based upon and claims the benefit of priority from prior U.S. Provisional Application No. 62/793,551, filed on Jan. 17, 2019 and Japanese patent application No. 2019-035995, filed on Feb. 28, 2019, the entire contents of which are incorporated herein by reference.

TECHNICAL FIELD

The present invention relates to a power supply unit for an aerosol inhaler.

BACKGROUND ART

There is available an aerosol inhaler that includes an aerosol generation source, a load for generating an aerosol from the aerosol generation source, a power supply able to discharge power to the load, and a control unit for controlling the power supply (for example, see Patent Literatures 1 to 4).
[Patent Literature 1] CN 206865186 U
[Patent Literature 2] CN 104348214 A
[Patent Literature 3] US 2017/0250552 A1
[Patent Literature 4] US 2015/0173124 A1

Since an aerosol inhaler is frequently used, charging and discharging of a power supply of the aerosol inhaler can be performed frequently.

For this reason, during charging and discharging, it is required to restrain the temperature of the power supply from rising and restrain heat from being concentrated in a circuit board or a specific circuit element, as much as possible.

Patent Literatures 1 to 4 are not considering any method of restraining the temperature of a power supply from rising.

An object of the present invention is to provide a power supply unit for an aerosol inhaler capable of restraining the temperature of a power supply from rising and restraining heat from being concentrated in a circuit board or a specific circuit element.

SUMMARY OF INVENTION

According to an aspect of the invention, there is provided a power supply unit for an aerosol inhaler, the power supply unit comprising: a power supply able to discharge power to a load for generating an aerosol from an aerosol generation source; a first circuit board including a resistor; and a second circuit board disposed apart from the first circuit board, and electrically connected to the first circuit board, wherein the second circuit board includes at least one of: a control device configured to be able to control at least one of discharging and charging of the power supply; and a charging device configured to convert power which is input, into charging power for the power supply.

DESCRIPTION OF EMBODIMENTS

Hereinafter, a power supply unit for an aerosol inhaler according to an embodiment of the present invention will be described. First of all, an aerosol inhaler equipped with the power supply unit will be described with reference to FIG. 1 and FIG. 2.

Aerosol Inhaler

Figure 1:
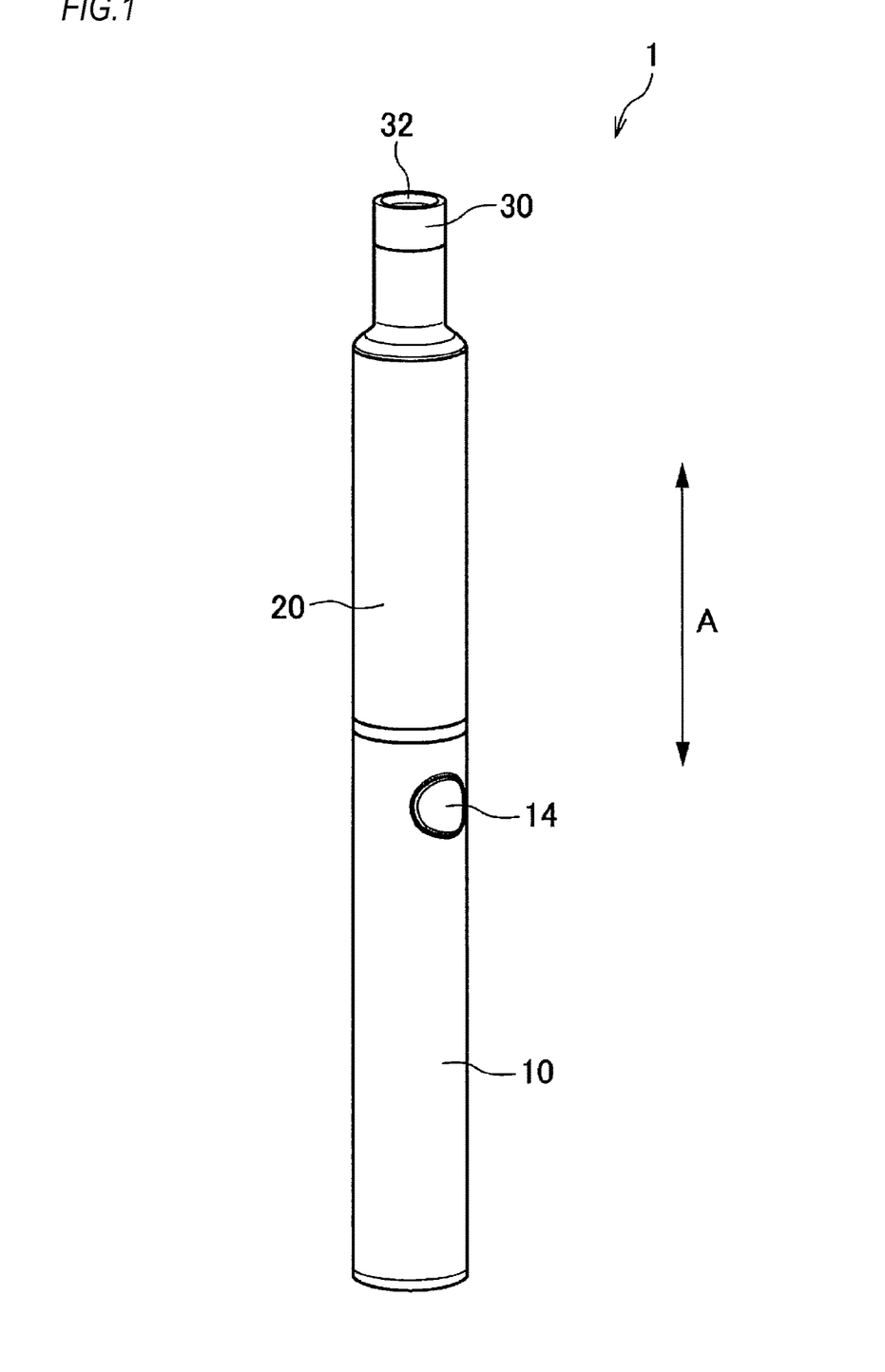
FIG. 1 is a perspective view of an aerosol inhaler equipped with a power supply unit of an embodiment of the present invention.
Figure 2:
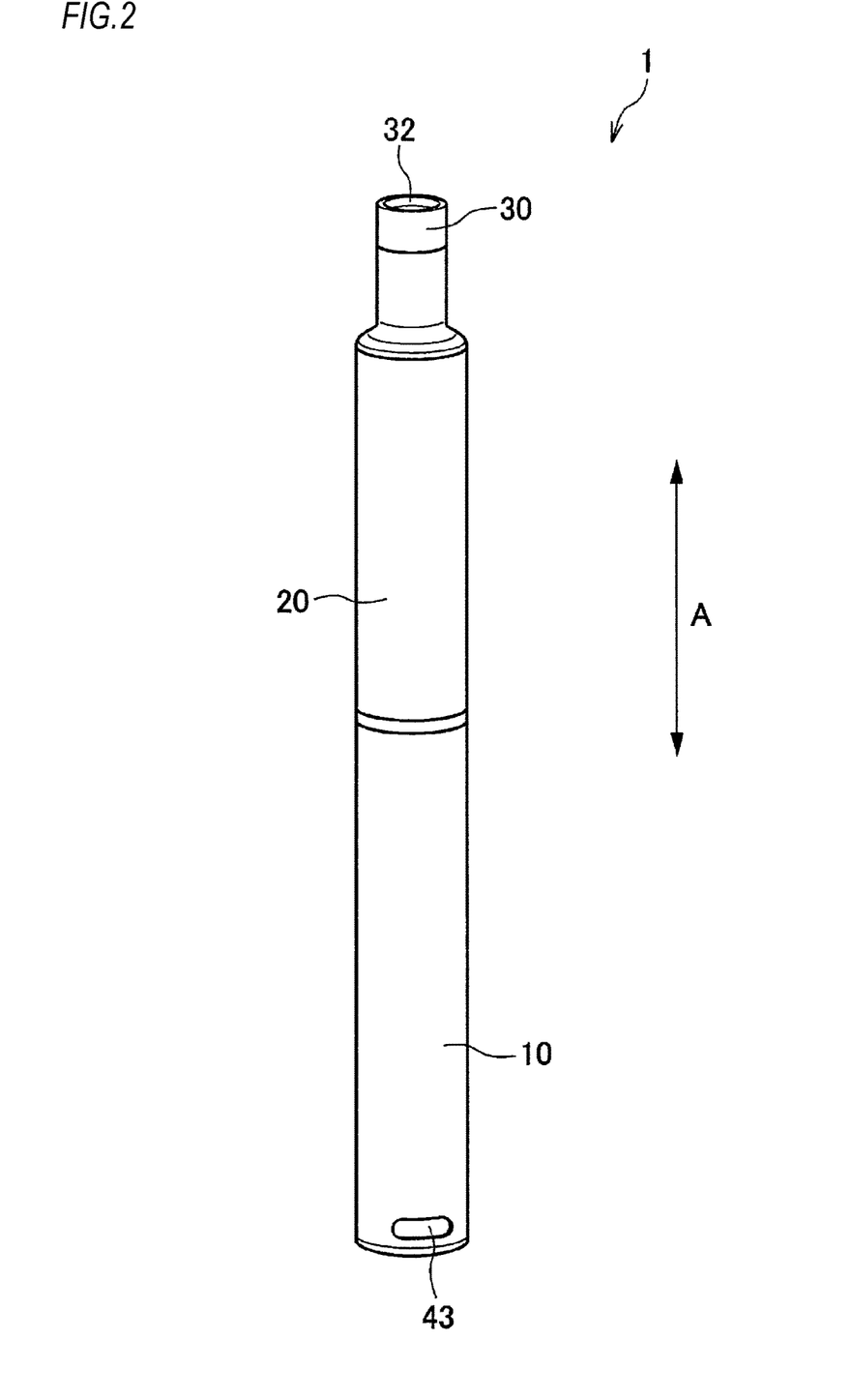
FIG. 2 is another perspective view of the aerosol inhaler of FIG. 1.

An aerosol inhaler 1 is a device for inhaling an aerosol containing a flavor without combustion, and has a rod shape extending along a certain direction (hereinafter, referred to as the longitudinal direction A). The aerosol inhaler 1 includes a power supply unit 10, a first cartridge 20, and a second cartridge 30 which are arranged in the order along the longitudinal direction A. The first cartridge 20 can be attached to and detached from the power supply unit 10. The second cartridge 30 can be attached to and detached from the first cartridge 20. In other words, the first cartridge 20 and the second cartridge 30 can be individually replaced.

Power Supply Unit

Figure 3:
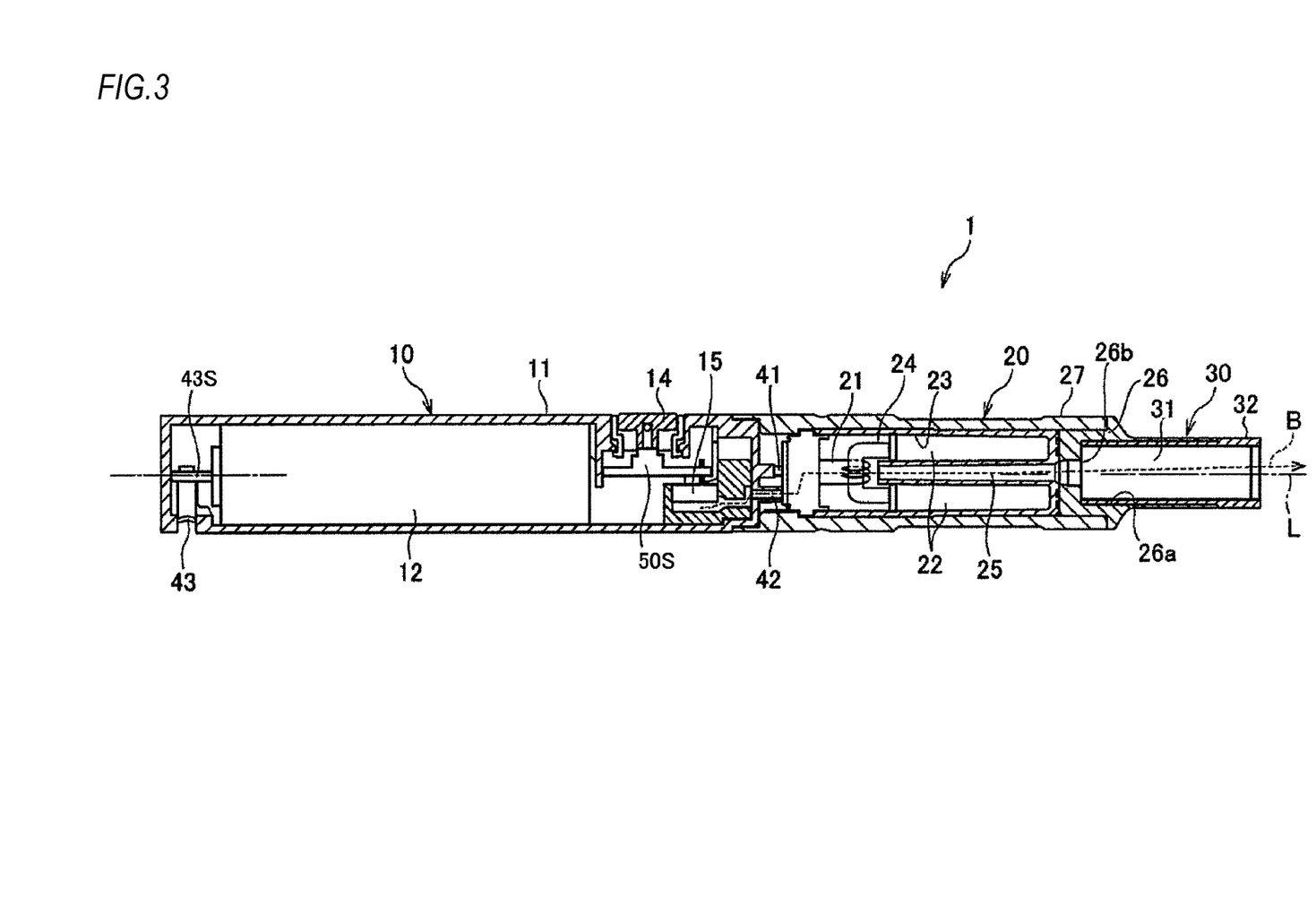
FIG. 3 is a cross-sectional view of the aerosol inhaler of FIG. 1.
Figure 4:
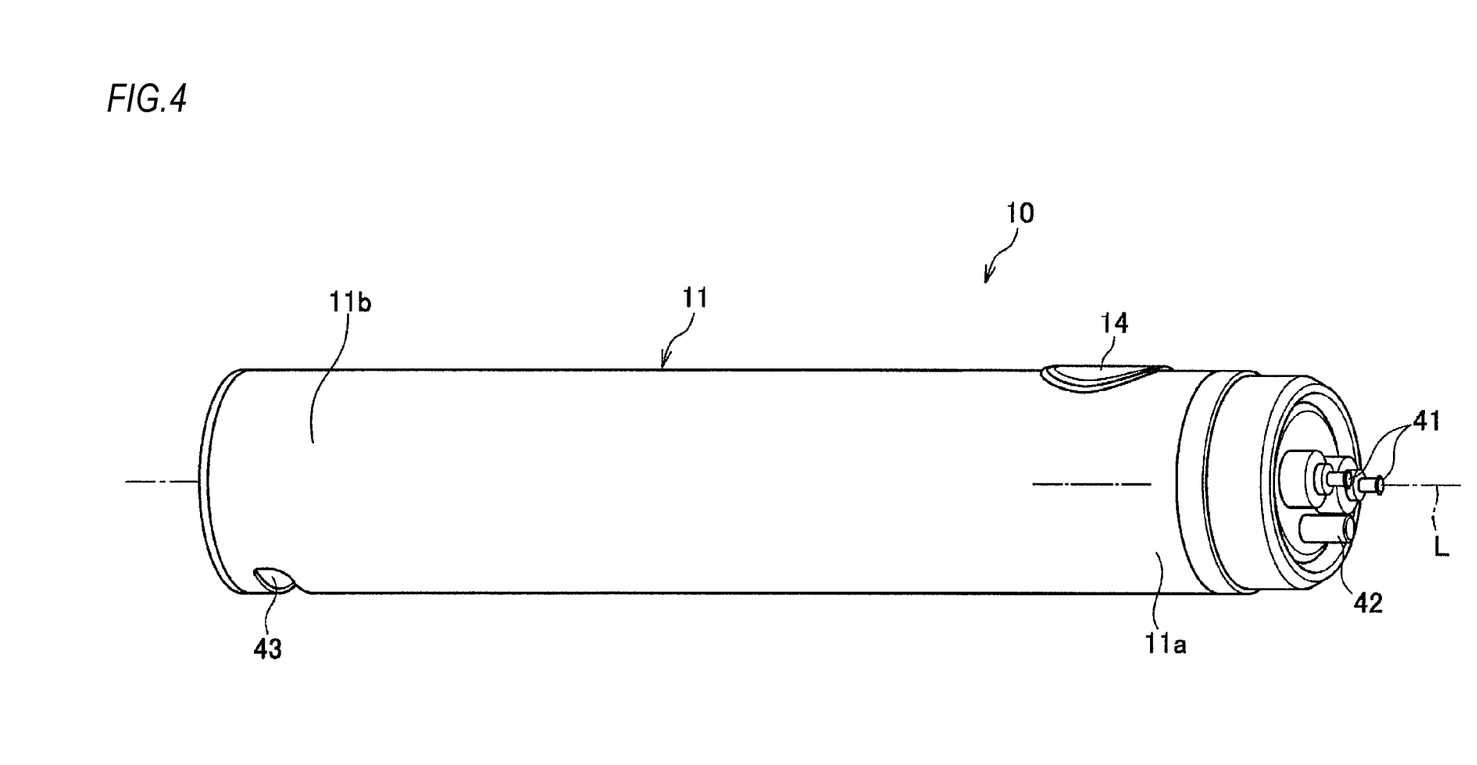
FIG. 4 is a perspective view of the power supply unit in the aerosol inhaler of FIG. 1.

The power supply unit 10 of the present embodiment includes a first circuit board 43S having a charging terminal 43 and a resistor 43R formed thereon (see FIG. 3, FIG. 5, and FIG. 7), a second circuit board 50S having a power supply 12 (see FIG. 3, and FIGS. 5 to 7), a charging IC (Integrated Circuit) 55, an MCU (Micro Controller Unit) 50, a switch 19, various sensors, and so on formed thereon (see FIG. 3, FIG. 5, and FIG. 7), and an FPC (Flexible Printed Circuits) board 13S (see FIG. 5 and FIG. 7), inside a cylindrical power supply unit case 11 (see FIG. 3 and FIG. 4). The power supply 12 is a chargeable secondary battery, an electric double-layer capacitor, or the like, and is preferably a lithium-ion battery. The external appearance of the power supply 12 is a pillar shape, such as a columnar shape or a prismatic shape, extending along a longitudinal direction A.

As shown in FIG. 4, on a top part 11a of the power supply unit case 11 positioned on one end side in the longitudinal direction A (the first cartridge (20) side), a discharging terminal 41 is provided. The discharging terminal 41 is provided so as to protrude from the top surface of the top part 11a toward the first cartridge 20, and is configured to be able to be electrically connected to a load 21 of the first cartridge 20. Further, on a part of the top surface of the top part 11a in the vicinity of the discharging terminal 41, an air supply part 42 for supplying air to the load 21 of the first cartridge 20 is provided.

Also, on a bottom part 11b of the power supply unit case 11 positioned on the other end side in the longitudinal direction A (the opposite side to the first cartridge 20), the charging terminal 43 able to be electrically connected to an external power supply, and the first circuit board 43S having the charging terminal 43 mounted thereon are provided. The charging terminal 43 is provided on the side surface of the bottom part 11b, and is a connector to which, for example, at least one of USB terminals, micro USB terminals, and lightning terminals (registered as a trade mark) can be connected.

Alternatively, the charging terminal 43 may be a power receiving part able to receive power from an external power supply in a non-contact manner. In this case, the charging terminal 43 (the power receiving part) may be composed of a power receiving coil. The wireless power transfer system may be an electromagnetic induction type, or may be a magnetic resonance type. Also, the charging terminal 43 may be a power receiving part able to receive power from an external power supply without any contact point. As another example, the charging terminal 43 may be configured such that at least one of USB terminals, micro USB terminals, and lightning terminals can be connected thereto and the above-mentioned power receiving part is included therein.

Figure 5:
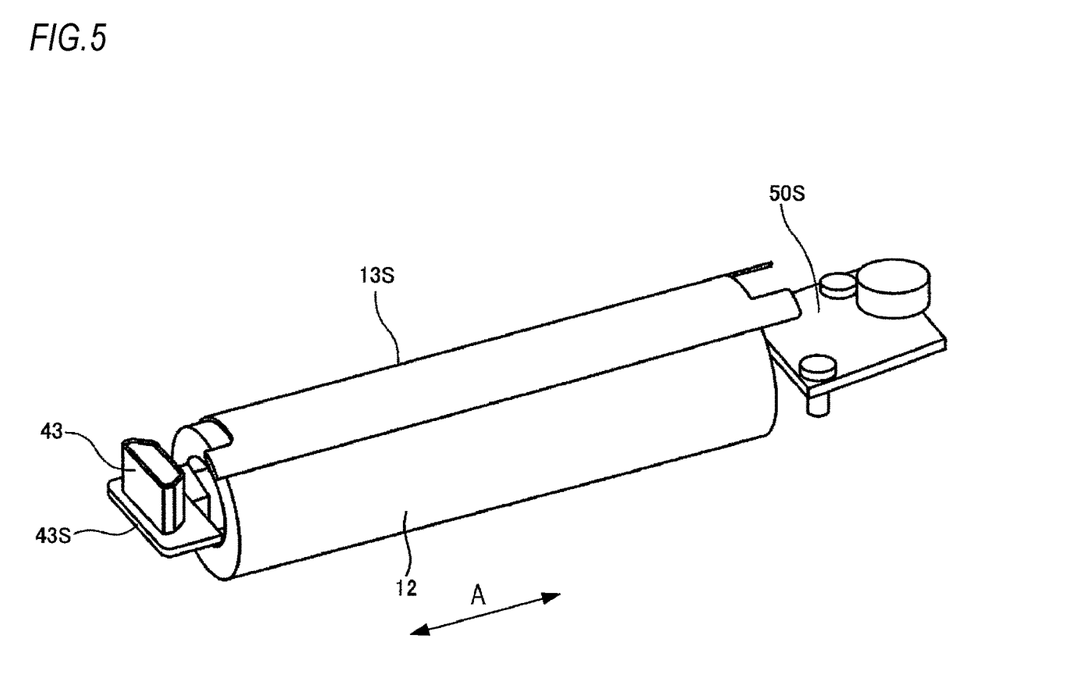
FIG. 5 is a perspective view illustrating a power supply, a first circuit board, a second circuit board, and an FPC board which are included inside the power supply unit in the aerosol inhaler of FIG. 1.

As shown in FIG. 5, the first circuit board 43S is disposed adjacent to one end part of the power supply 12 in the longitudinal direction A (on the opposite side to the first cartridge (20) side). The surface of this end part constitutes a surface closest to the first circuit board 43S. Also, the second circuit board 50S is disposed adjacent to the other end part of the power supply 12 in the longitudinal direction A (on the first cartridge (20) side). The surface of this end part constitutes a surface closest to the second circuit board 50S. As described above, the first circuit board 43S and the second circuit board 50S are disposed apart from each other, and they are electrically connected by the FPC board 13S.

As shown in FIG. 4, on the side surface of the top part 11a of the power supply unit case 11, an operation unit 14 which the user can operate is provided so as to face the opposite side to the charging terminal 43. More specifically, the operation unit 14 and the charging terminal 43 are symmetric with respect to the point of intersection of a straight line connecting the operation unit 14 and the charging terminal 43 and the center line of the power supply unit 10 in the longitudinal direction A. The operation unit 14 is composed of a button type switch, a touch panel, or the like. As shown in FIG. 3, in the vicinity of the operation unit 14, an inhalation sensor 15 for detecting puff actions are provided.

Figure 6:
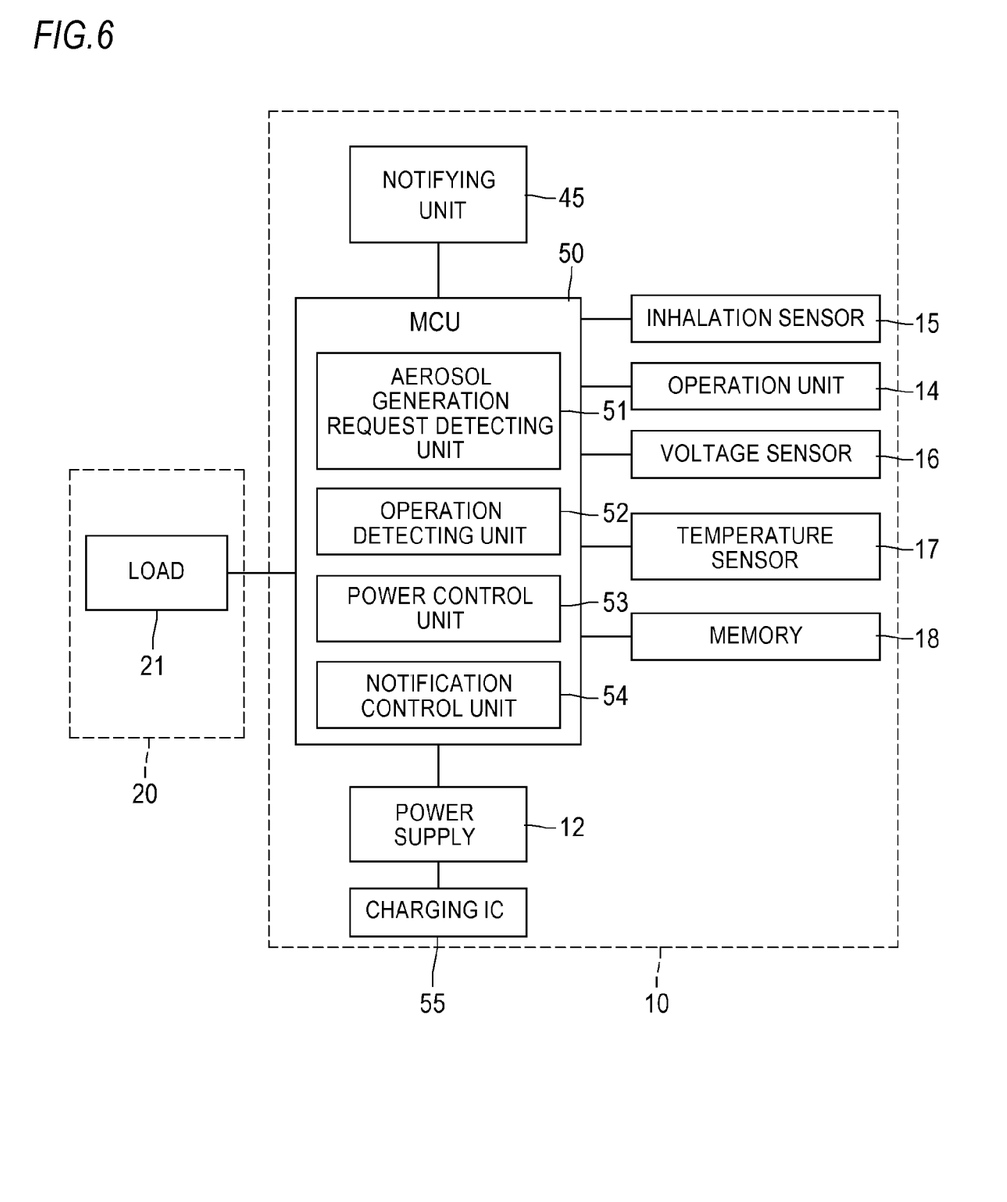
FIG. 6 is a block diagram illustrating the main part configuration of the power supply unit in the aerosol inhaler of FIG. 1.
Figure 7:
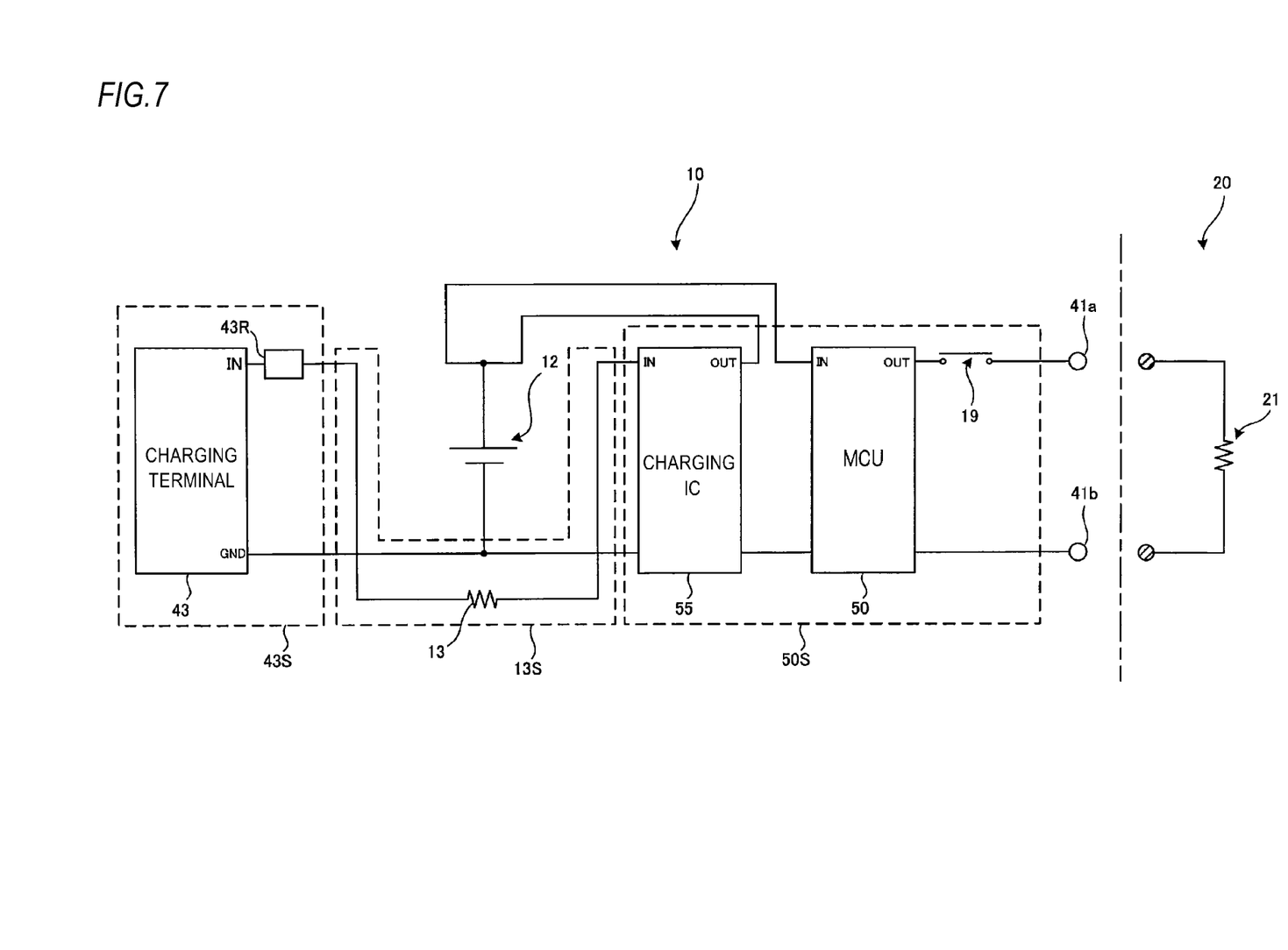
FIG. 7 is a schematic diagram illustrating the circuit configuration of the power supply unit in the aerosol inhaler of FIG. 1.

The charging IC 55 shown in FIG. 6 and FIG. 7 performs control to convert power which is input from an external power supply to the charging terminal 43 into charging power for the power supply 12 and supply the power to the power supply 12. The charging IC 55 is configured with an LDO (Low-Dropout Regulator) for dropping input voltage and outputting the dropped voltage.

The MCU 50 is connected to various sensor devices such as the inhalation sensor 15 for detecting puff (inhaling) actions, a voltage sensor 16 for measuring the power-supply voltage of the power supply 12, and a temperature sensor 17 for measuring the temperature of the power supply 12, the operation unit 14, a notifying unit 45, and a memory 18 for storing the number of puff actions, the time for which power has been applied to the load 21, and so on, as shown in FIG. 6, and performs a variety of control on the aerosol inhaler 1. The MCU 50 is specifically a processor.

Also, in the power supply unit case 11, an air intake (not shown in the drawings) for taking in air is formed. The air intake may be formed around the operation unit 14, or may be formed around the charging terminal 43.

First Cartridge

As shown in FIG. 3, the first cartridge 20 includes a reservoir 23 for storing an aerosol source 22, the electric load 21 for atomizing the aerosol source 22, a wick 24 for drawing the aerosol source from the reservoir 23 toward the load 21, an aerosol channel 25 for an aerosol generated by atomizing the aerosol source 22 to flow toward the second cartridge 30, an end cap 26 for storing a part of the second cartridge 30, inside a cylindrical cartridge case 27.

The reservoir 23 is formed so as to surround the aerosol channel 25, and holds the aerosol source 22. In the reservoir 23, a porous member such as a resin web or cotton may be stored, and the porous member may be impregnated with the aerosol source 22. The aerosol source 22 includes a liquid such as glycerin, propylene glycol, or water.

The wick 24 is a liquid holding member for drawing the aerosol source 22 from the reservoir 23 toward the load 21 using capillarity, and is configured with, for example, glass fiber, a porous ceramic, or the like.

The load 21 atomizes the aerosol source 22, without combustion, by power which is supplied from the power supply 12 through the discharging terminal 41. The load 21 is configured with a heating wire wound with a predetermined pitch (a coil). However, the load 21 needs only to be an element capable of atomizing the aerosol source 22, thereby generating an aerosol, and is, for example, a heating element or an ultrasonic wave generator. Examples of the heating element include a heating resistor, a ceramic heater, an induction heating type heater, and so on.

The aerosol channel 25 is provided on the downstream side of the load 21 on the center line L of the power supply unit 10.

The end cap 26 includes a cartridge storage part 26a for storing a part of the second cartridge 30, and a connecting passage 26b for connecting the aerosol channel 25 and the cartridge storage part 26a.

Second Cartridge

The second cartridge 30 holds a flavor source 31. An end part of the second cartridge 30 on the first cartridge (20) side is stored in the cartridge storage part 26a provided in the end cap 26 of the first cartridge 20, so as to be able to be removed. Another end part of the second cartridge 30 on the opposite side to the first cartridge (20) side is configured as an inhalation port 32 for the user. However, the inhalation port 32 does not necessarily need to be configured integrally with the second cartridge 30 so as not to be separable from the second cartridge, and may be configured to be able to be attached to and detached from the second cartridge 30. If the inhalation port 32 is configured separately from the power supply unit 10 and the first cartridge 20 as described above, it is possible to keep the inhalation port 32 sanitary.

The second cartridge 30 adds a flavor to the aerosol generated by atomizing the aerosol source 22 by the load 21, by passing the aerosol through the flavor source 31. As a raw material piece which constitutes the flavor source, a compact made by forming shredded tobacco or a tobacco raw material into a grain shape can be used. The flavor source 31 may be configured with plants (such as mint, herbal medicines, herbs) other than tobacco. To the flavor source 31, a flavoring agent such as menthol may be added.

The aerosol inhaler 1 of the present embodiment can generate an aerosol containing the flavor by the aerosol source 22, the flavor source 31, and the load 21. In other words, the aerosol source 22 and the flavor source 31 constitute an aerosol generation source for generating an aerosol.

The aerosol generation source in the aerosol inhaler 1 is a part which the user can replace to use. For this part, for example, one first cartridge 20 and one or more (for example, five) second cartridges 30 can be provided as one set to the user.

The configuration of the aerosol generation source which can be used in the aerosol inhaler 1 is not limited to the configuration in which the aerosol source 22 and the flavor source 31 are configured separately, and may be a configuration in which the aerosol source 22 and the flavor source 31 are formed integrally, a configuration in which the flavor source 31 is omitted and the aerosol source 22 contains a substance which can be contained in the flavor source 31, a configuration in which the aerosol source 22 contains a medical substance or the like instead of the flavor source 31, or the like.

In the aerosol inhaler 1 configured as described above, as shown by an arrow B in FIG. 3, air entering from the intake (not shown in the drawings) formed in the power supply unit case 11 passes through the air supply part 42, and passes near the load 21 of the first cartridge 20. The load 21 atomizes the aerosol source 22 drawn from the reservoir 23 by the wick 24. The aerosol generated by atomizing flows through the aerosol channel 25 together with the air entering from the intake, and is supplied to the second cartridge 30 through the connecting passage 26b. The aerosol supplied to the second cartridge 30 passes through the flavor source 31, whereby the flavor is added, and is supplied to the inhalation port 32.

Also, in the aerosol inhaler 1, the notifying unit 45 for notifying a variety of information is provided (see FIG. 6). The notifying unit 45 may be configured with a light emitting element, or may be configured with a vibrating element, or may be configured with a sound output element. The notifying unit 45 may be a combination of two or more elements of light emitting elements, vibrating elements, and sound output elements. The notifying unit 45 may be provided in any one of the power supply unit 10, the first cartridge 20, and the second cartridge 30; however, it is preferable that the notifying unit be provided in the power supply unit 10. For example, the area around the operation unit 14 is configured to have translucency to permit light which is emitted by light emitting elements such as LEDs to pass through.

Electric Circuit

Now, the details of the electric circuit of the power supply unit 10 will be described with reference to FIG. 7 and FIG. 8.

The power supply unit 10 includes the power supply 12, the first circuit board 43S having a positive electrode side discharging terminal 41a and a negative electrode side discharging terminal 41b which constitute the discharging terminal 41, the charging terminal 43, and the resistor 43R formed thereon, the second circuit board 50S having the charging IC 55, the MCU 50, and the switch 19 formed thereon, and the FPC board 13S electrically connecting the first circuit board 43S and the second circuit board 50S. Also, a resistor 13 shown in FIG. 7 indicates interconnection resistance which is caused by wiring included in the FPC board 13S.

The resistor 43R is configured with an element having a resistance value, such as a resistive element or a transistor, and one end thereof is connected to an input terminal IN of the charging terminal 43. Another end part (the other end) of the resistor 43R on the opposite side to the charging terminal (43) side is electrically connected to an input terminal IN of the charging IC 55 through the wiring formed in the FPC board 13S. Also, a ground terminal GND of the charging terminal 43 is electrically connected to the negative electrode side discharging terminal 41b through the wiring in the FPC board 13S. To the wiring which connects the ground terminal GND of the charging terminal 43 and the negative electrode side discharging terminal 41b, a negative electrode side terminal of the power supply 12, a ground terminal of the charging IC 55, and a ground terminal of the MCU 50 are connected.

An output terminal OUT of the charging IC 55 is electrically connected to a positive electrode side terminal of the power supply 12. To the positive electrode side terminal of the power supply 12, the input terminal IN of the MCU 50 is connected. Between the output terminal OUT of the MCU 50 and the positive electrode side discharging terminal 41a, the switch 19 is disposed. The switch 19 is composed of, for example, a semiconductor element such as a MOSFET, and is turned on and off under the control of the MCU 50.

In the electric circuit of the power supply unit 10 shown in FIG. 7, the switch 19 is provided between the positive electrode side of the power supply 12 and the positive electrode side discharging terminal 41a. Instead of this so-called plus control type, the switch 19 may be a minus control type which is provided between the negative electrode side discharging terminal 41b and the negative electrode side of the power supply 12.

Figure 8:
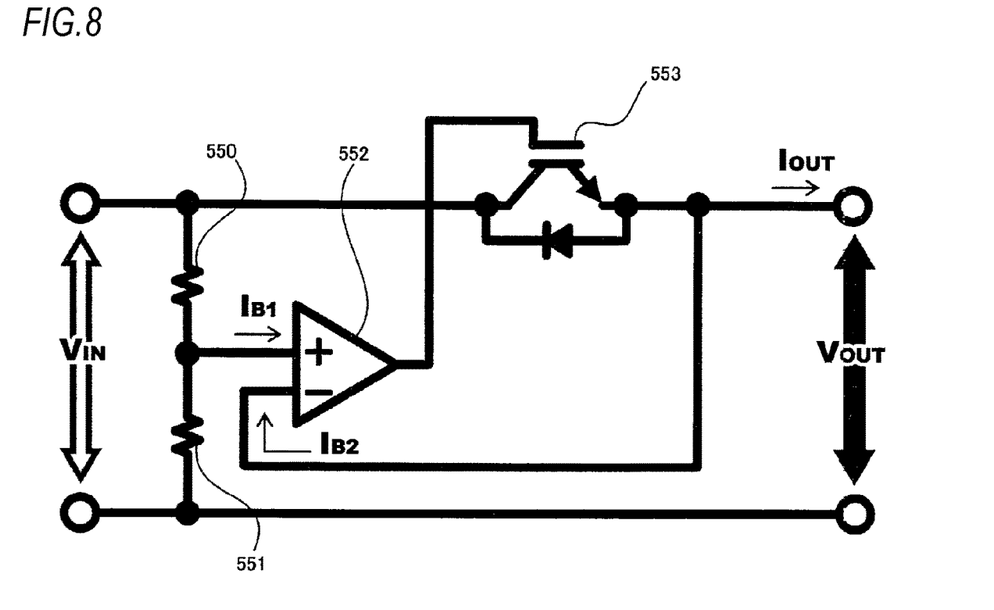
FIG. 8 is a circuit diagram illustrating an internal configuration example of a charging IC shown in FIG. 7.

As shown in FIG. 8, the charging IC 55 includes an FET (Field Effect Transistor) 553 connected between the input terminal IN and the output terminal OUT, a series circuit of a resistor 550 and a resistor 551 connected in parallel with the input terminal IN, and a comparator 552 having a non-inverting input terminal which is connected to the connection point between the resistor 550 and the resistor 551 and an inverting input terminal which is connected to the output of the FET 553. In other words, the charging IC 55 includes a linear regulator connected between the input terminal IN and the output terminal OUT. The gate voltage of the FET 553 is controlled by the comparator 552 such that the output voltage and output current of the FET 553 become target values (here, it is assumed as an example that the target values are 4.2 V and 460 mA which are used to control charging of general lithium-ion batteries).

The charging IC 55 having the configuration shown in FIG. 8 performs dropping of the input voltage using a power loss in the FET 553. When a power loss in the FET 553 is represented by $\Delta W$, and the input voltage of the charging IC 55 is represented by $V_{IN}$, and the output voltage of the charging IC 55 is represented by $V_{OUT}$, and the output current of the charging IC 55 is represented by $I_{OUT}$, and bias current which is input to the non-inverting input terminal of the comparator 552 is represented by $I_{B1}$, and bias current which is input to the inverting input terminal of the comparator 552 is represented by $I_{B2}$, the following Expression (A) is established.

$$\Delta W = (V_{IN} - V_{OUT}) \cdot I_{OUT} + V_{OUT} \cdot (I_{B1} + I_{B2}) \quad (A)$$

Here, since the second term of the right side in Expression (A) is sufficiently smaller than the first term of the right side in Expression (A), Expression (A) can be approximated to the following Expression (B). Therefore, the charging IC 55 can be considered as consuming power of $\Delta W$ shown in Expression (B), of the power which is input.

$$\Delta W = (V_{IN} - V_{OUT}) \cdot I_{OUT} \quad (B)$$

MCU

As shown in FIG. 6, the MCU 50 includes an aerosol generation request detecting unit 51, an operation detecting unit 52, a power control unit 53, and a notification control unit 54, as functional blocks which are realized by executing a program.

The aerosol generation request detecting unit 51 detects a request for aerosol generation based on the output result of the inhalation sensor 15. The inhalation sensor 15 is configured to output the value of a variation in the pressure in the power supply unit 10 (the internal pressure) caused by inhalation of the user through the inhalation port 32. The inhalation sensor 15 is, for example, a pressure sensor for outputting an output value (for example, a voltage value or a current value) according to the internal pressure which varies according to the flow rate of air which is sucked from the intake (not shown in the drawings) toward the inhalation port 32 (i.e. a puff action of the user). The inhalation sensor 15 may be configured with a capacitor microphone or the like.

The operation detecting unit 52 detects operations which are performed on the operation unit 14 by the user.

The notification control unit 54 controls the notifying unit 45 such that the notifying unit notifies a variety of information. For example, the notification control unit 54 controls the notifying unit 45 in response to detection of a timing to replace the second cartridge 30, such that the notifying unit notifies the timing to replace the second cartridge 30. The notification control unit 54 detects and notifies a timing to replace the second cartridge 30, based on the number of puff actions or the cumulative time for which power has been supplied to the load 21, stored in the memory 18. The notification control unit 54 is not limited to notification of a timing to replace the second cartridge 30, and may notify a timing to replace the first cartridge 20, a timing to replace the power supply 12, a timing to charge the power supply 12, and so on.

The power control unit 53 controls discharging of the power supply 12 through the discharging terminal 41 by switching on and off the switch 19, if the aerosol generation request detecting unit 51 detects the request for aerosol generation. The power control unit 53 performs control such that the amount of aerosol which is generated by atomizing the aerosol source by the load 21 falls in a desired range, i.e. such that the amount of power which is supplied from the power supply 12 to the load 21 falls in a predetermined range.

Specifically, the power control unit 53 controls switching on and off of the switch 19 by, for example, PWM (Pulse Width Modulation) control. Alternatively, the power control unit 53 may control switching on and off of the switch 19 by PFM (Pulse Frequency Modulation) control.

The power control unit 53 needs only to perform control on at least discharging of the power supply 12; however, it also may perform control on charging of the power supply 12. For example, if the aerosol generation request is detected when the charging IC 55 is charging the power supply 12, the power control unit 53 may perform control on discharging of the power supply 12 while performing control to stop the charging IC 55 charging the power supply 12. Also, if the state of charge of the power supply 12 reaches a predetermined state when the charging IC 55 is charging the power supply 12, the power control unit 53 may perform control to end the charging.

Power Supply Charging Operation

The operation of the aerosol inhaler 1 having the above-described configuration during charging of the power supply 12 will be described.

If a charging cable is connected to the charging terminal 43, and this charging cable is connected to an external power supply, charging of the power supply 12 is started.

Hereinafter, as an example, a charging operation which is performed in the case where the input voltage of the charging terminal 43 is 5.15 V, and the input current of the charging terminal 43 is 500 mA, and the resistance value of the resistor 43R is 1Ω, and the resistance value of the resistor 13 which is the interconnection resistance of the FPC board 13S is 24 mΩ will be described.

If the current of 500 mA flows in the input terminal IN of the charging terminal 43, in the resistor 43R, a voltage drop of 0.5 V (=500 mA×1Ω) occurs. Therefore, the voltage to be input to the FPC board 13S becomes 4.65 V (=5.15−0.5). Also, in the FPC board 13S, a voltage drop of 500 mA×24 mΩ, i.e. about 0.01 V is caused by the resistor 13 (having the resistance value of 24 mΩ). Therefore, the input voltage $V_{IN}$ to be input to the charging IC 55 becomes 4.64 V (=4.65−0.01). Therefore, in the charging IC 55, the input voltage is dropped by 0.44 V such that the output voltage $V_{OUT}$ becomes 4.2 V.

Figure 9:
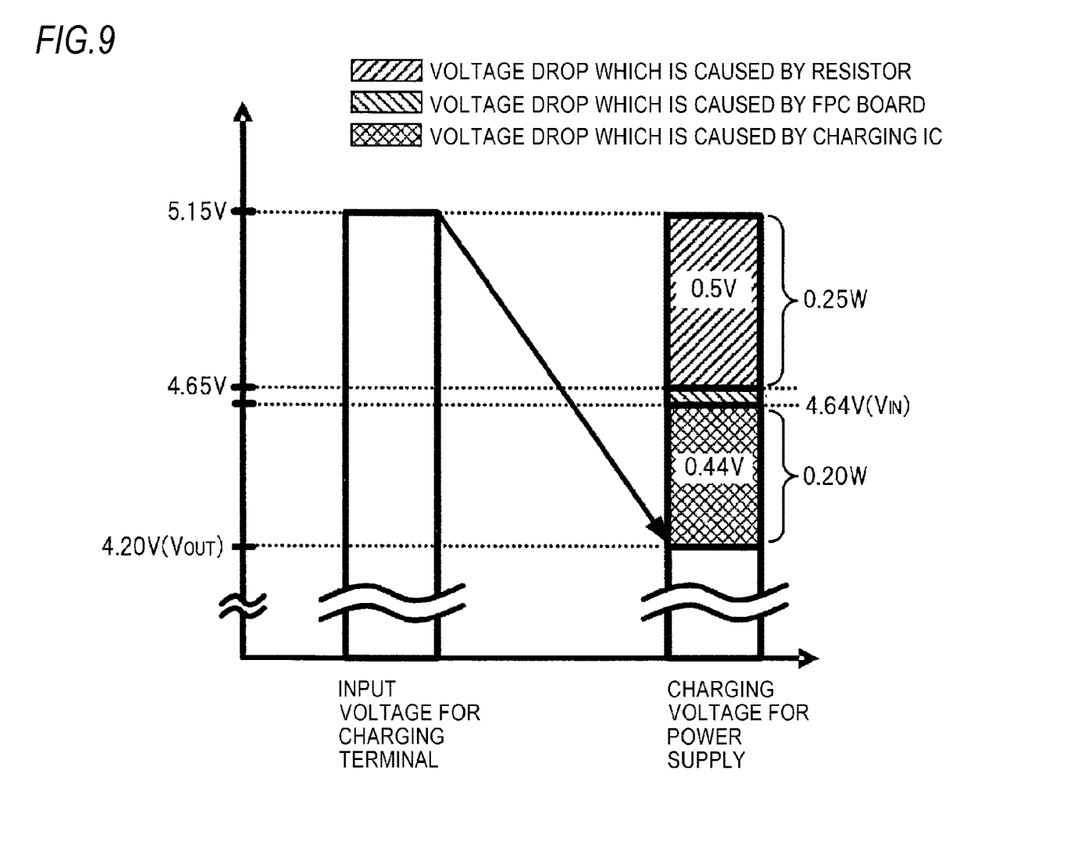
FIG. 9 is a view illustrating change in voltage which is input to a charging terminal during charging of the power supply shown in FIG. 7.

FIG. 9 is a view illustrating change in voltage which is input to the charging terminal 43 during charging of the power supply 12. As shown in FIG. 9, in the first circuit board 43S, since the voltage drop of 0.5 V is caused by the resistor 43R, power of 0.25 W (=0.5 V×500 mA) is consumed. Also, in the second circuit board 50S, since the voltage drop of 0.44 V occurs in the charging IC 55, power of 0.44 V×460 mA, i.e. about 0.20 W is consumed.

Here, as a comparative example, it can be considered the case where the resistor 43R of the first circuit board 43S does not exist in the circuit configuration shown in FIG. 7. In this case, since a voltage drop does not occur in the first circuit board 43S, power is not consumed. Meanwhile, in the second circuit board 50S, since a voltage drop of 0.94 V (=(5.15−0.01)−4.2), power of 0.94 V×460 mA, i.e. about 43.2 W is consumed.

According to the configuration of the power supply unit 10 shown in FIG. 7, a part of power which can be consumed in the charging IC 55 having the configuration of the above-mentioned comparative example can be consumed in the first circuit board 43S positioned apart from the second circuit board 50S. In other words, in the power supply unit 10, each of the first circuit board 43S and the second circuit board 50S positioned apart from each other generates heat and disperses the heat. Therefore, in the power supply unit 10, as compared to the comparative example in which the heat generation sources are concentrated in one place in the power supply unit 10, it is possible to prevent unevenness of heat in the power supply unit 10, and it is possible to restrain the temperature of the power supply 12 from rising. Therefore, it is possible to suppress deterioration of the power supply 12, thereby extending the life of the device. Furthermore, since the heat generation sources are retrained from being concentrated on the second circuit board 50S, it is possible to protect the elements provided on the second circuit board 50S, such as the charging IC 55 and the MCU 50. Also, since the resistance value of the resistor 551 on the FPC board 13S is the interconnection resistance, and is a very small value, the amount of heat generation is such small that it is negligible, and thermal influence of the resistor on the power supply 12 is minor.

As described above, from the viewpoint of preventing unevenness of heat in the power supply unit 10, it can be said that it is preferable to set the resistance value of the resistor 43R to such a value that the amounts of heat generation of the first circuit board 43S and the second circuit board 50S during charging of the power supply 12 become substantially equal. The case where two amounts of heat generation are substantially equal means the case where the difference between the two amounts of heat generation is equal to or smaller than 10% (preferably, 5%) of each of the amounts of heat generation.

By the way, on the first circuit board 43S, as an element which generates heat, only the resistor 43R is provided. However, on the second circuit board 50S, a plurality of elements which generates heat, such as the charging IC 55 and the MCU 50 is provided. Therefore, in the second circuit board 50S, the ratio of the amount of heat which is generated by the charging IC 55 and the MCU 50 is large.

For this reason, the resistance value of the resistor 43R is set to such a value that the amount of power consumption of the resistor 43R during charging of the power supply 12 and the sum of the amounts of power consumption of the charging IC 55 and the MCU 50 during charging of the power supply 12 become substantially equal. In this case, it is possible to easily realize the configuration making the amounts of heat generation of the first circuit board 43S and the second circuit board 50S during charging of the power supply 12 substantially equal. The case where two amounts of power consumption are substantially equal means the case where the difference between the two amounts of power consumption is equal to or smaller than 10% (preferably, 5%) of each of the amounts of power consumption.

Moreover, in the second circuit board 50S, the amount of heat generation of the charging IC 55 is largest. For this reason, it is desired to set the resistance value of the resistor 43R to such a value that the amount of power consumption of the resistor 43R during charging of the power supply 12 becomes larger than the amount of power consumption of the charging IC 55 during charging of the power supply 12.

Specifically, when the resistance value of the resistor 43R is represented by R, and current which is input from the charging terminal 43 is represented by $I_{IN}$, and voltage which is input from the charging terminal 43 is represented by $V_{BUS}$, and the resistance value of the resistor 13 is represented by $R_{FPC}$, the resistance value of the resistor 43R needs only to be set such that the relation of the following Expression (C) is satisfied. Since Expression (D) can be obtained by transforming Expression (C), the resistance value of the resistor 43R may be determined such that Expression (D) is satisfied. In this case, it is possible to make the amount of power consumption of the resistor 43R during charging of the power supply 12 larger than the amount of power consumption of the charging IC 55 during charging of the power supply 12.

$$R \cdot I_{IN}^2 > \{V_{BUS} - (R + R_{FPC}) \cdot I_{IN} - V_{OUT}\} \cdot I_{OUT} \qquad \text{Expression (C)}$$

$$R > (V_{BUS} - V_{OUT} - R_{FPC} \cdot I_{IN}) \cdot I_{OUT} / (I_{IN} + I_{OUT}) \cdot I_{IN} \qquad \text{Expression (D)}$$

Also, in this case, it is possible to easily realize the configuration making the amount of power consumption of the resistor 43R during charging of the power supply 12 and the sum of the amounts of power consumption of the charging IC 55 and the MCU 50 during charging of the power supply 12 substantially equal, and the configuration making the amounts of heat generation of the first circuit board 43S and the second circuit board 50S during charging of the power supply 12 substantially equal.

Also, for the charging IC 55, a minimum input voltage necessary to output 4.2 V which is the target value of the charging voltage for the power supply 12 is determined as a minimum operation guarantee voltage. Therefore, it is required to determine an upper limit value for the resistance value of the resistor 43R such that voltage which is input to the charging IC 55 does not become lower than the minimum operation guarantee voltage. In other words, the resistor 43R needs to have a resistance value required to drop the voltage which is supplied from an external power supply to a value larger than the minimum operation guarantee voltage of the charging IC 55.

If it is assumed that the minimum operation guarantee voltage of charging ICs 55 which are generally used is, for example, 4.4 V, a value (=1.38Ω) which is obtained by subtracting a voltage drop (in the above-mentioned example, 0.01 V) attributable to the resistor 13 of the FPC board 13S and the above-mentioned minimum operation guarantee voltage from voltage which is input to the charging terminal 43 (in the above-mentioned example, 5.15 V) becomes an upper limit value for the resistance value of the resistor 43R.

Also, if the resistance value of the resistor 43R is set in a range between 1Ω and 1.38Ω, in designing various voltages, currents, and voltage values described above, it is possible to optimize the heat balance in the power supply unit 10, and restrain the temperature of the power supply 12 from rising.

Also, when the power-supply voltage of the power supply 12 is lower than the minimum operation guarantee voltage of the MCU 50, the MCU 50 may receive power from an external power supply, and operate. In this case, the resistor 43R needs to have a resistance value for dropping the voltage which is supplied from the external power supply to a value larger than the minimum operation guarantee voltage of the charging IC 55 and larger than the minimum operation guarantee voltage of the MCU 50.

When the distance from the first circuit board 43S to the power supply 12 and the distance from the second circuit board 50S to the power supply 12 are substantially equal, as described above, by making the amounts of heat generation of the first circuit board 43S and the second circuit board 50S during charging substantially equal, it is possible to make the amounts of heat to be given to the power supply 12 by the first circuit board 43S and the second circuit board 50S substantially equal.

However, due to some factors such as restrictions in arranging various members in the power supply unit 10, it may be impossible to make the distance from the first circuit board 43S to the power supply 12 and the distance from the second circuit board 50S to the power supply 12 equal. In this case, it is preferable to determine the amounts of heat generation of the first circuit board 43S and the second circuit board 50S during charging, in view of the difference between the two distances.

For example, a value which is obtained by dividing the amount of power consumption (or heat generation) of the first circuit board 43S during charging by the square of the distance from the first circuit board 43S to the power supply 12 is defined as the amount of heat which the first circuit board 43S gives to the power supply 12 during charging. Also, a value which is obtained by dividing the amount of power consumption (or heat generation) of the second circuit board 50S during charging by the square of the distance from the second circuit board 50S to the power supply 12 is defined as the amount of heat which the second circuit board 50S gives to the power supply 12 during charging. In this case, the resistance value of the resistor 43R is set to such a value that the amounts of heat of the two circuit boards become equal. Then, amounts of heat substantially equal are given from the first circuit board 43S and the second circuit board 50S to the power supply 12. Therefore, it is possible to prevent unevenness of heat in the power supply unit 10, and restrain the temperature of the power supply 12 from rising.

In the case where the charging IC 55 uses a switching regulator in place of the linear regulator, the resistance value of the resistor 43R may be set based on a loss in the switching regulator during charging. As examples of the loss in the switching regulator, a transition loss, a conduction loss, a switching loss, and so on can be taken.

Until now, the example in which the resistance value of the resistor 43R is set to such a value that it is possible to make two parameters (the amounts of heat generation, the amounts of power consumption, or the amounts of heat) during charging of the power supply 12 close has been described. In the aerosol inhaler 1, it also is possible to perform discharging of the power supply 12 while charging the power supply 12.

For this reason, the resistance value of the resistor 43R may be set to such a value that in the case of performing charging and discharging of the power supply 12 at the same time, the amounts of heat generation or power consumption of the first circuit board 43S and the second circuit board 50S become substantially equal, or the amount of heat which is given to the power supply 12 by the first circuit board 43S and the amount of heat which is given to the power supply 12 by the second circuit board 50S become substantially equal.

Also, in the aerosol inhaler 1, in a state where an external power supply and the charging IC 55 are connected, it also is possible to perform only discharging of the power supply 12 without performing charging of the power supply 12. For this reason, the resistance value of the resistor 43R may be set to such a value that in the case of performing discharging of the power supply 12, the amounts of heat generation or power consumption of the first circuit board 43S and the second circuit board 50S become substantially equal, or the amount of heat which is given to the power supply 12 by the first circuit board 43S and the amount of heat which is given to the power supply 12 by the second circuit board 50S become substantially equal.

Figure 10:
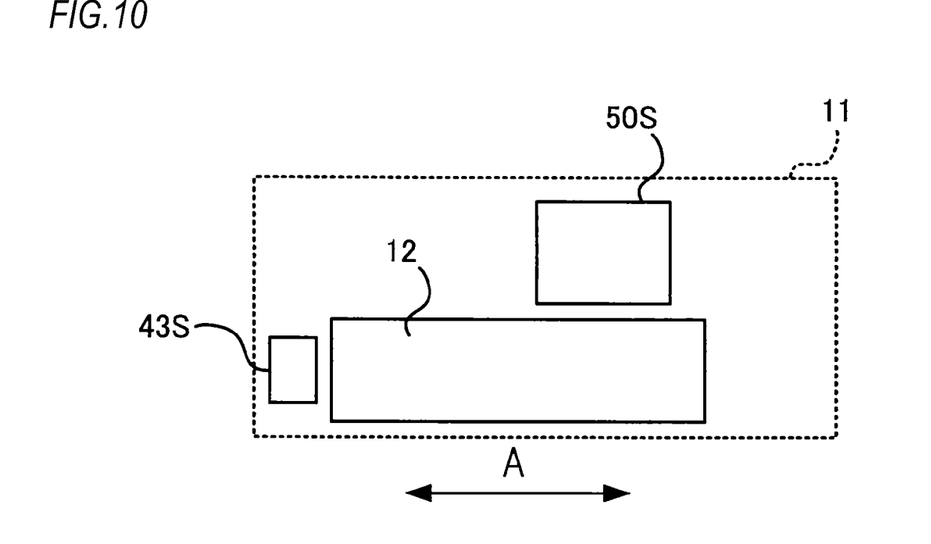
FIG. 10 is a schematic diagram illustrating a first modification of the arrangement of the first circuit board and the second circuit board relative to the power supply in the power supply unit.

FIG. 10 is a schematic diagram illustrating a first modification of the arrangement of the first circuit board 43S and the second circuit board 50S relative to the power supply 12 in the power supply unit 10. FIG. 10 is a view illustrating the power supply 12, the first circuit board 43S, and the second circuit board 50S as seen from a direction perpendicular to the longitudinal direction A of the power supply unit 10. In the example of FIG. 10, the second circuit board 50S is different from that in FIG. 5 in that it is disposed adjacent to one end part of the power supply 12 in the transverse direction. Also, in FIG. 10, the positions of the first circuit board 43S and the second circuit board 50S may be reversed. Even in the arrangement example shown in FIG. 10, similarly in FIG. 5, the first circuit board 43S and the second circuit board 50S which are heat sources are disposed close to the different surfaces of the power supply 12. Therefore, it is possible to restrain the power supply 12 from being locally heated.

Also, in the case where there is a difference between the amounts of heat generation of the first circuit board 43S and the second circuit board 50S during charging, in the arrangement example of FIG. 10, it is preferable to dispose a circuit board which generates a larger amount of heat during charging, at the position of the second circuit board 50S. In this case, a wide surface of the power supply 12 receives heat which is generated by the circuit board which can generate a larger amount of heat. Therefore, it is possible to restrain the power supply 12 from being locally heated, and extend the life of the power supply 12.

Figure 11:
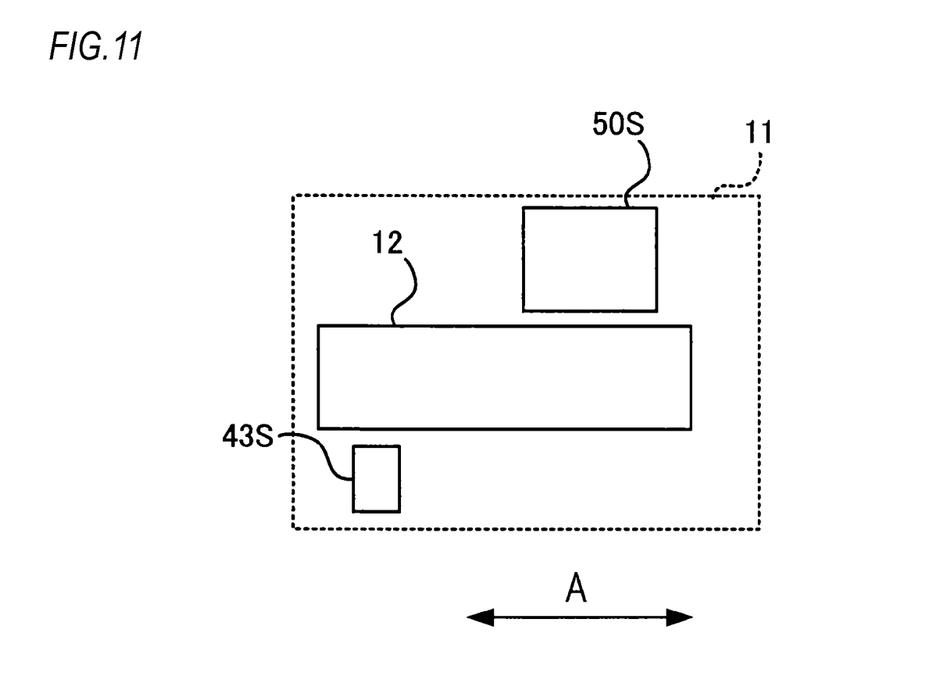
FIG. 11 is a schematic diagram illustrating a second modification of the arrangement of the first circuit board and the second circuit board relative to the power supply in the power supply unit.

FIG. 11 is a schematic diagram illustrating a second modification of the arrangement of the first circuit board 43S and the second circuit board 50S relative to the power supply 12 in the power supply unit 10. FIG. 11 is a view illustrating the power supply 12, the first circuit board 43S, and the second circuit board 50S as seen from a direction perpendicular to the longitudinal direction A of the power supply unit 10. In the example of FIG. 11, the first circuit board 43S is different from that in FIG. 10 in that it is disposed adjacent to the other end part of the power supply 12 in the transverse direction. Even in the arrangement example shown in FIG. 11, similarly in FIG. 5, the first circuit board 43S and the second circuit board 50S which are heat sources are disposed close to the different surfaces of the power supply 12. Therefore, it is possible to restrain the power supply 12 from being locally heated. From the viewpoint of restraining the power supply 12 from being locally heated, it is preferable that the first circuit board 43S and the second circuit board 50S should be disposed to be offset in the longitudinal direction of the power supply unit 10.

The above description has been made on the assumption of the configuration in which the charging IC 55 is set in the power supply unit 10; however, the idea of the present invention can also be applied to other configurations. For example, in the power supply unit 10 shown in FIG. 7, the charging IC 55 may be set inside a charging cable which is connected to the charging terminal 43, and the MCU 50 may perform control on charging and discharging of the power supply 12. Even in this configuration, since there is the resistor 43R connected in series with the charging terminal 43, the operation of the MCU 50 for performing control on charging and discharging causes heat generation of the second circuit board 50S and heat generation of the first circuit board 43S. Therefore, it is possible to restrain the power supply 12 from being locally heated, and extend the life of the power supply 12.

In this specification, at least the following inventions (1) to (18) are disclosed. Moreover, although the corresponding constituent elements and the like in the embodiments described above are shown in parentheses, it is not limited thereto.

(1) A power supply unit (the power supply unit 10) for an aerosol inhaler (the aerosol inhaler 1), the power supply unit comprising:
   a power supply (the power supply 12) able to discharge power to a load (load 21) for generating an aerosol from an aerosol generation source;

a first circuit board (the first circuit board 43S) including a resistor (43R); and a second circuit board (the second circuit board 50S) disposed apart from the first circuit board, and electrically connected to the first circuit board, wherein the second circuit board includes at least one of: a control device (the MCU 50) configured to be able to control at least one of discharging and charging of the power supply; and a charging device (the charging IC 55) configured to convert power which is input, into charging power for the power supply.

According to (1), in the case where power is supplied to the first circuit board and the second circuit board, since each of the first circuit board and the second circuit board generates heat, it is possible to prevent unevenness of heat in the power supply unit, and restrain the temperature of the power supply from rising. Therefore, it is possible to suppress deterioration of the power supply, and extend the life of the device. Moreover, it is possible to suppress concentration of heat into a specific circuit board or circuit element. As a result, the power supply unit has an energy saving effect that it is possible to maximize the period when it is possible to use the power supply without replacing the power supply with a new one.

(2) The power supply unit according to (1), wherein at least one of the charging device and the control device is provided only on the second circuit board.

According to (2), since at least one of the charging device and the control device likely to generate large amounts of heat is provided only on the second circuit board, the amount of heat generation of the second circuit board is likely to be large. Even in this configuration, since each of the first circuit board and the second circuit board generates heat, it is possible to prevent unevenness of heat in the power supply unit, and restrain the temperature of the power supply from rising.

(3) The power supply unit according to (1) or (2), wherein the first circuit board includes a connector (the charging terminal 43) to which an external power supply can be electrically connected, and the resistor is connected in series with the connector.

According to (3), it is possible to drop the voltage which is input from the connector by the resistor and supply it to the second circuit board. Therefore, it becomes possible to suppress heat generation of the second circuit board. As a result, it is possible to protect the charging device or the control device, and the other elements provided on the second circuit board, from heat.

(4) The power supply unit according to any one of (1) to (3), wherein the second circuit board includes the charging device.

According to (4), since the second circuit board includes the charging device, the amount of heat generation of the second circuit board is likely to be large. In this configuration, since power which needs to be consumed in the charging device is consumed by the resistor of the first circuit board, it is possible to suppress heat generation of the charging device. As a result, it is possible to suppress heat generation of the second circuit board.

(5) The power supply unit according to any one of (1) to (4), wherein the resistor has such a resistance value that amounts of heat generation of the first circuit board and the second circuit board during charging of the power supply become substantially equal.

According to (5), since the resistor makes the amounts of heat generation of the first circuit board and the second circuit board substantially equal, it is possible to prevent unevenness of heat in the power supply unit, and restrain the temperature of the power supply from rising.

(6) The power supply unit according to any one of (1) to (4), wherein the second circuit board includes the charging device, and the resistor has such a resistance value that an amount of power consumption of the resistor during charging of the power supply becomes larger than an amount of power consumption of the charging device during charging of the power supply.

According to (6), since it is possible to reduce the amount of power consumption of the charging device during charging of the power supply, it is possible to reduce heat generation of the second circuit board attributable to the charging device. Also, since it is possible to reduce the amount of power consumption of the charging device, even though other elements which consume power are provided on the second circuit board, it is possible to maintain a balance in heat generation between the first circuit board and the second circuit board, and it is possible to prevent unevenness of heat in the power supply unit. Also, the other elements provided on the second circuit board are restrained from being damaged by heat.

(7) The power supply unit according to (6), wherein the second circuit board further includes the control device.

According to (7), even in the case where the control device generates heat, it is possible to maintain a balance in heat generation between the first circuit board and the second circuit board, and it is possible to prevent unevenness of heat in the power supply unit. Also, the control device is restrained from being damaged by heat.

(8) The power supply unit according to any one of (1) to (4), wherein the second circuit board includes the charging device and the control device, and the resistor has such a resistance value that an amount of power consumption of the resistor during charging of the power supply becomes substantially equal to a sum of amounts of power consumption of the charging device and the control device during charging of the power supply.

According to (8), since the amount of power consumption of the resistor and the amount of power consumption of the charging device and the control device become equal, it is possible to maintain a balance in heat generation between the first circuit board and the second circuit board, and it is possible to prevent unevenness of heat in the power supply unit.

(9) The power supply unit according to any one of (1) to (4), wherein the first circuit board includes a connector (the charging terminal 43) to which an external power supply can be electrically connected, and the resistor has a resistance value for dropping voltage which is supplied by the external power supply to a value larger than a minimum operation guarantee voltage of the charging device or the control device.

According to (9), voltage dropping of the resistor is performed such that that the dropped voltage does not fall below the minimum operation guarantee voltage. Therefore, it becomes possible to input the minimum operation guarantee voltage to the charging device or the control device, and it is possible to make the charging device or the control device sufficiently function.

(10) The power supply unit according to any one of (1) to (4), wherein
the resistor has a resistance value between 1Ω and 1.38Ω.

According to (10), since there is the specific condition for the resistance value obtained experimentally and analytically on the assumption of charging devices or control devices which are generally used, is possible to prevent unevenness of heat in the power supply unit.

(11) The power supply unit according to (10), wherein
the resistance value is 1Ω.

According to (11), it becomes possible to reduce the size and the cost.

(12) The power supply unit according to any one of (1) to (11), wherein
a surface of the power supply closest to the first circuit board is different from a surface of the power supply closest to the second circuit board.

According to (12), it is possible to restrain the power supply from being locally heated.

(13) The power supply unit according to any one of (1) to (11), wherein
the first circuit board is provided on one end side of the power supply in a longitudinal direction, and
the second circuit board is provided on the other end side of the power supply in the longitudinal direction.

According to (13), it is possible to restrain the power supply from being locally heated.

(14) The power supply unit according to any one of (1) to (11), wherein
the first circuit board is provided at one of end parts of the power supply in a longitudinal direction and a transverse direction, and
the second circuit board is provided at the other of the end parts of the power supply in the longitudinal direction and the transverse direction.

According to (14), it is possible to restrain the power supply from being locally heated.

(15) The power supply unit according to (14), wherein
one of the first circuit board and the second circuit board which generates a larger amount of heat is provided at the end part of the power supply in the transverse direction.

According to (15), it is possible to restrain the power supply from being locally heated.

(16) A power supply unit (the power supply unit 10) for an aerosol inhaler (the aerosol inhaler 1), the power supply unit comprising:
a power supply (the power supply 12) able to discharge power to a load (load 21) for generating an aerosol from an aerosol generation source;
a first circuit board (the first circuit board 43S); and
a second circuit board (the second circuit board 50S) disposed apart from the first circuit board, and electrically connected to the first circuit board,
wherein amounts of heat generation of the first circuit board and the second circuit board during at least one of charging and discharging of the power supply are substantially equal.

According to (16), in the case where power is supplied to the first circuit board and the second circuit board, since the first circuit board and the second circuit board generate amounts of heat substantially equal, it is possible to prevent unevenness of heat in the power supply unit, and restrain the temperature of the power supply from rising. Therefore, it is possible to suppress deterioration of the power supply, and extend the life of the device. Moreover, it is possible to suppress concentration of heat into a specific circuit board or circuit element. As a result, the power supply unit has an energy saving effect that it is possible to maximize the period when it is possible to use the power supply without replacing the power supply with a new one.

(17) A power supply unit (the power supply unit 10) for an aerosol inhaler (the aerosol inhaler 1), the power supply unit comprising:
a power supply (the power supply 12) able to discharge power to a load (load 21) for generating an aerosol from an aerosol generation source;
a first circuit board (the first circuit board 43S); and
a second circuit board (the second circuit board 50S) disposed apart from the first circuit board, and electrically connected to the first circuit board,
wherein, during at least one of charging and discharging of the power supply, a total amount of power consumption of elements of the first circuit board and a total amount of power consumption of elements of the second circuit board are substantially equal.

According to (17), in the case where power is supplied to the first circuit board and the second circuit board, since the first circuit board and the second circuit board consume amounts of power substantially equal, it is possible to prevent unevenness of heat in the power supply unit, and restrain the temperature of the power supply from rising. Therefore, it is possible to suppress deterioration of the power supply, and extend the life of the device. Moreover, it is possible to suppress concentration of heat into a specific circuit board or circuit element. As a result, the power supply unit has an energy saving effect that it is possible to maximize the period when it is possible to use the power supply without replacing the power supply with a new one.

(18) A power supply unit (the power supply unit 10) for an aerosol inhaler (the aerosol inhaler 1), the power supply unit comprising:
a power supply (the power supply 12) able to discharge power to a load (load 21) for generating an aerosol from an aerosol generation source;
a first circuit board (the first circuit board 43S); and
a second circuit board (the second circuit board 50S) disposed apart from the first circuit board, and electrically connected to the first circuit board,
wherein, during at least one of charging and discharging of the power supply, an amount of heat which the first circuit board gives to the power supply and an amount of heat which the second circuit board gives to the power supply are substantially equal.

According to (18), in the case where power is supplied to the first circuit board and the second circuit board, since amounts of heat substantially equal are given from the first circuit board and the second circuit board to the power supply, it is possible to prevent unevenness of heat in the power supply unit, and restrain the temperature of the power supply from rising. Therefore, it is possible to suppress deterioration of the power supply, and extend the life of the device. Moreover, it is possible to suppress concentration of heat into a specific circuit board or circuit element. As a result, the power supply unit has an energy saving effect that it is possible to maximize the period when it is possible to use the power supply without replacing the power supply with a new one.

What is claimed is:

1. A power supply unit for an aerosol inhaler, the power supply unit comprising:
   a power supply able to discharge power to a load for generating an aerosol from an aerosol generation source;
   a first circuit board including a resistor; and
   a second circuit board disposed apart from the first circuit board, and electrically connected to the first circuit board,
   wherein the second circuit board includes at least one of: a control device configured to be able to control at least one of discharging and charging of the power supply; and a charging device configured to convert power which is input, into charging power for the power supply, and
   wherein one end of the resistor is electrically connected to an input terminal of the control device or the charging device included in the second circuit board in series.

2. The power supply unit according to claim 1, wherein at least one of the charging device and the control device is provided only on the second circuit board.

3. The power supply unit according to claim 1, wherein the first circuit board includes a connector to which an external power supply can be electrically connected, and
   the resistor is connected in series with the connector.

4. The power supply unit according to claim 1, wherein the second circuit board includes the charging device.

5. The power supply unit according to claim 1, wherein the resistor has such a resistance value that amounts of heat generation of the first circuit board and the second circuit board during charging of the power supply become subsequently equal.

6. The power supply unit according to claim 1, wherein the second circuit board includes the charging device, and
   the resistor has such a resistance value that an amount of power consumption of the resistor during charging of the power supply becomes larger than an amount of power consumption of the charging device during charging of the power supply.

7. The power supply unit according to claim 6, wherein the second circuit board further includes the control device.

8. The power supply unit according to claim 1, wherein the second circuit board includes the charging device and the control device, and
   the resistor has such a resistance value that an amount of power consumption of the resistor during charging of the power supply becomes subsequently equal to a sum of amounts of power consumption of the charging device and the control device during charging of the power supply.

9. The power supply unit according to claim 1, wherein the first circuit board includes a connector to which an external power supply can be electrically connected, and
   the resistor has a resistance value for dropping voltage which is supplied by the external power supply to a value larger than a minimum operation guarantee voltage of the charging device or the control device.

10. The power supply unit according to claim 1, wherein the resistor has a resistance value between $1\Omega$ and $1.38\Omega$.

11. The power supply unit according to claim 10, wherein the resistance value is $1\Omega$.

12. The power supply unit according to claim 1, wherein a surface of the power supply closest to the first circuit board is different from a surface of the power supply closest to the second circuit board.

13. The power supply unit according to claim 1, wherein the first circuit board is provided on one end side of the power supply in a longitudinal direction, and
    the second circuit board is provided on the other end side of the power supply in the longitudinal direction.

14. The power supply unit according to claim 1, wherein the first circuit board is provided at one of end parts of the power supply in a longitudinal direction and a transverse direction, and
    the second circuit board is provided at the other of the end parts of the power supply in the longitudinal direction and the transverse direction.

15. The power supply unit according to claim 14, wherein one of the first circuit board and the second circuit board which generates a larger amount of heat is provided at the end part of the power supply in the transverse direction.

16. A power supply unit for an aerosol inhaler, the power supply unit comprising:
    a power supply able to discharge power to a load for generating an aerosol from an aerosol generation source;
    a first circuit board including a resistor; and
    a second circuit board disposed apart from the first circuit board, and electrically connected to the first circuit board via the resistor in series,
    wherein amounts of heat generation of the first circuit board and the second circuit board during at least one of charging and discharging of the power supply are substantially equal.

17. A power supply unit for an aerosol inhaler, the power supply unit comprising:
    a power supply able to discharge power to a load for generating an aerosol from an aerosol generation source;
    a first circuit board including a resistor; and
    a second circuit board disposed apart from the first circuit board, and electrically connected to the first circuit board via the resistor in series,
    wherein, during at least one of charging and discharging of the power supply, a total amount of power consumption of elements of the first circuit board and a total amount of power consumption of elements of the second circuit board are subsequently equal.

18. A power supply unit for an aerosol inhaler, the power supply unit comprising:
    a power supply able to discharge power to a load for generating an aerosol from an aerosol generation source;
    a first circuit board including a resistor; and
    a second circuit board disposed apart from the first circuit board, and electrically connected to the first circuit board via the resistor in series,
    wherein, during at least one of charging and discharging of the power supply, an amount of heat which the first circuit board gives to the power supply and an amount of heat which the second circuit board gives to the power supply are substantially equal.

* * * * *